(12) United States Patent
Nakajima et al.

(10) Patent No.: US 11,241,249 B2
(45) Date of Patent: Feb. 8, 2022

(54) ENDOSCOPIC SNARE

(71) Applicants: OSAKA UNIVERSITY, Osaka (JP); HAKKO CO., LTD., Nagano (JP)

(72) Inventors: Kiyokazu Nakajima, Osaka (JP); Masaomi Agatsuma, Nagano (JP); Hidenori Takagi, Nagano (JP); Shun Nitta, Nagano (JP)

(73) Assignee: HAKKO CO., LTD., Nagano (JP)

( * ) Notice: Subject to any disclaimer, the term of this patent is extended or adjusted under 35 U.S.C. 154(b) by 540 days.

(21) Appl. No.: 15/421,546

(22) Filed: Feb. 1, 2017

(65) Prior Publication Data

US 2017/0215911 A1    Aug. 3, 2017

(30) Foreign Application Priority Data

Feb. 3, 2016   (JP) .............................. JP2016-018568

(51) Int. Cl.
*A61B 17/3205*    (2006.01)
*A61B 17/00*      (2006.01)
*A61B 18/14*      (2006.01)

(52) U.S. Cl.
CPC .. *A61B 17/32056* (2013.01); *A61B 17/00234* (2013.01); *A61B 18/1492* (2013.01);
(Continued)

(58) Field of Classification Search
CPC ........ A61B 17/32056; A61B 17/00234; A61B 18/1492; A61B 2017/00358; A61B 2018/141
See application file for complete search history.

(56) References Cited

U.S. PATENT DOCUMENTS 2,856,933 A * 10/1958 Hildebrand ...... A61B 17/32056
606/113
3,903,892 A *  9/1975 Komiya ............. A61B 1/00098
606/110
(Continued)

FOREIGN PATENT DOCUMENTS

JP    2001292960 A    10/2001
JP    2010505450 A     2/2010
(Continued)

OTHER PUBLICATIONS

Office Action in CN Application No. 201710063752.6 dated Nov. 5, 2018, 5 pages.

*Primary Examiner* — Jing Rui Ou
(74) *Attorney, Agent, or Firm* — Marshall, Gerstein & Borun LLP (57) ABSTRACT

There is provided an endoscopic snare including: a flexible sheath 1; a cable 2 configured to slide in the sheath; a snare loop 3 connected to the cable 2, and projecting from or retracting into the sheath 1; a distal end tip 4 disposed in a distal end part of the sheath and retaining the snare loop 3; and a hand operating part for operating the snare loop 3 via the cable 2. One end of the snare loop 3 is attached to the distal end tip and the other end of the snare loop 3 is attached to a distal end of the cable. The snare loop 3 is expanded into a ring shape without a protruding portion when it is projected from the sheath 1, and is formed into an asymmetric shape where expansion is deviated to either side about an axis of the sheath.

4 Claims, 7 Drawing Sheets

(52) U.S. Cl.
CPC ............... *A61B 2017/00358* (2013.01); *A61B 2018/141* (2013.01)

(56) References Cited

U.S. PATENT DOCUMENTS

| | | | | |
|---|---|---|---|---|
| 4,181,131 | A * | 1/1980 | Ogiu | A61B 18/14 606/47 |
| 4,325,374 | A * | 4/1982 | Komiya | A61B 18/14 606/47 |
| 4,643,187 | A * | 2/1987 | Okada | A61B 18/14 606/47 |
| 5,613,973 | A * | 3/1997 | Jackson | A61B 17/0218 606/1 |
| 5,738,683 | A * | 4/1998 | Osypka | A61B 5/0422 606/47 |
| 5,836,947 | A * | 11/1998 | Fleischman | A61B 18/1492 606/47 |
| 6,142,994 | A * | 11/2000 | Swanson | A61B 18/1482 606/41 |
| 6,152,922 | A | 11/2000 | Ouchi | |
| 6,416,505 | B1 * | 7/2002 | Fleischman | A61B 18/1482 606/1 |
| 9,345,539 | B2 * | 5/2016 | Yanuma | A61B 18/1492 |
| 2003/0023237 | A1 * | 1/2003 | Mollenauer | A61B 18/085 606/27 |
| 2004/0092953 | A1 * | 5/2004 | Salameh | A61B 18/14 606/113 |
| 2011/0034804 | A1 * | 2/2011 | Hubregtse | A61M 25/0082 600/433 |
| 2011/0087247 | A1 * | 4/2011 | Fung | A61B 17/0469 606/148 |
| 2015/0032119 | A1 * | 1/2015 | Kuroda | A61B 17/221 606/113 |

FOREIGN PATENT DOCUMENTS

| | | |
|---|---|---|
| WO | WO-2008/044615 A1 | 4/2008 |
| WO | WO-2013/103934 A1 | 7/2013 |
| WO | 2015/004420  * | 1/2015 |

* cited by examiner

ENDOSCOPIC SNARE

CROSS-REFERENCE TO RELATED APPLICATION

This application is based upon and claims the benefit of priority of the prior Japanese Patent Application No. 2016-018568, filed on Feb. 3, 2016, the entire contents of which are incorporated herein by reference.

BACKGROUND OF THE INVENTION (1) Field of the Invention

The present invention relates to an endoscopic snare that is inserted into a body through a forceps channel of an endoscope, and captures and excises tissues such as a polyp.

(2) Description of Related Art

A general endoscopic snare that is inserted into a forceps channel of an endoscope and is used for excising a polyp is so configured that a wire loop is extensionally provided at a distal end of an operation wire inserted through a sheath, and the wire loop advances or retracts from the distal end of the sheath by advancement or retraction of the operation wire from the hand side. The wire loop projecting from the sheath expands into a ring shape by the self-elasticity, and a polyp is excised by capturing the polyp in this expanded wire loop and conducting high-frequency cauterization. The wire loop is memorized to be stored in its closed state in a thin sheath, and to expand when it is projected. The shape of the wire loop in the expanded state is an oval or polygonal shape that is long in the axial direction and short in the width direction in many cases. Since the configuration of gradually pushing out the expansion-memorized part is employed, the oblong tendency is more significant when the pushout length (projecting length) is shorter, and the wire loop is little expanded in the early stage of projection.

If the wire loop is oblong as described above, it is necessary to increase the pushout length so as to ensure a sufficient width for capturing a polyp. On the other hand, a large projecting length can hinder the operation, for example, due to the decreased stiffness of the wire at the time of capturing. This tendency is larger, particularly for a small polyp because expansion in the width direction of the wire loop is poor in the early stage of expansion.

Given these circumstances, as an endoscopic snare having a wire loop capable of expanding irrespectively of the magnitude of the projecting length from the sheath, and keeping the ring shape without becoming oblong as much as possible, the one in which the snare loop (wire loop) is provided with a plurality of outwardly projecting parts is proposed (Patent Document 1). In this endoscopic snare, by forming the snare loop to have a plane polygonal shape having three sides: first, second and third sides extending outward from the vicinity of the distal end of the snare loop, and a fourth side oriented in the narrowing direction in the rear of the three sides, in which the second side is the shortest and the fifth side is the longest, the snare loop expands even when the projecting length from the distal end of the sheath is short. Also proposed is a snare having an inward projecting portion formed at a predetermined position of the snare loop, which bends and projects in the inward direction of the snare loop and can come into engagement with a distal end part of the sheath in the withdrawing operation of the snare wire (Patent Document 2). In this endoscopic snare, by bringing the inward projecting portion into engagement with the distal end part of the sheath, the snare loop is guided and retained in an ideal curved loop shape capable of binding a polyp tightly.

CITATION LIST

Patent Literature

Patent Document 1: JP 2001-292960 A
Patent Document 2: JP 2010-505450 W

SUMMARY OF THE INVENTION

These endoscopic snares are described to be capable of expanding without being relatively narrowed in the width direction even when the projecting length of the snare loop from the sheath is short, and capable of effectively capturing a small polyp. All of these snare loops are projected in the direction parallel with the axis of the sheath, and expanded symmetrically. However, for expanding the snare loop to have a symmetric shape, and for retaining the shape of the expanded loop, it is necessary to provide a protruding portion in the center part of the distal end of the snare loop, and memorize the wire of the snare loop to largely open on both sides so that the snare loop is developed largely on both sides in the root part of the protruding portion. Even with such a shape, the expansion in the width direction is limited in the early stage of projection for the reason of structure, and it is difficult to form a ring shape in this stage.

Further, in general snare loops including the snares of the above documents, a protruding portion is provided at the distal end. Such a snare loop is developed symmetrically on both sides about the axis of the sheath, and the endoscopic channel into which the endoscopic snare is to be inserted is provided parallel with a camera. However, it is not necessarily the best measure that the snare loop is projected straight and symmetrically on both sides about the axis of the sheath. In other words, it would be better to design the snare loop to project on the extension of the axial line of the camera disposed in parallel rather than on the axial line of the sheath. Also, the protruding portion of the snare loop has a certain gap in its root part for the reason of structure. When the polyp is captured and the snare loop is squeezed, parts that are not in contact with the circumference of the polyp may be generated similarly to parts that are set parallel at a predetermined interval in the root part of the snare loop. This can lead nonuniformity in thermocauterectomy due to current-carrying failure in such parts.

In light of the above, it is an object of the present invention to form a loop that is less susceptible to the shape variation in an outline formed into a ring shape irrespectively of the magnitude of the projecting length of a snare loop when the snare loop is projected from a sheath, in an endoscopic snare for excising tissues such as a polyp via an endoscope. Also, it is an object of the present invention to provide an endoscopic snare that enables easy and stable capturing of a polyp irrespectively of the size of the polyp by capturing the polyp at the position that is easily viewable by an endoscopic camera.

It is also an object of the present invention to provide an endoscopic snare that enables secure and stable thermocauterectomy by bringing a current-carrying part into contact with the circumference of a polyp without any gap when the polyp is captured.

The endoscopic snare of the present invention includes a flexible sheath; a cable configured to slide in the sheath; a snare loop connected to the cable, and projecting from or retracting into the sheath; a distal end tip disposed in a distal end part of the sheath and retaining the snare loop; and a hand operating part for operating the snare loop via the cable. One end of the snare loop is attached to the distal end tip and the other end of the snare loop is attached to the cable distal end. The snare loop is expanded into a ring shape without a protruding portion when it is projected from the sheath, and is formed into an asymmetric shape deviated to either side about an axis of the sheath.

Preferably, the snare loop is formed of a metallic stranded wire, and a distal end surface of the distal end tip is disposed at the same position with a distal end of the sheath, or at a position within 5 mm from the distal end.

Operation

According to the endoscopic snare of the aforementioned solution, the snare loop is formed of a metallic stranded wire that is rich in self restoring force, and less likely to cause creases and deformation. Also, one end of the snare loop is retained by the distal end tip disposed in the distal end part of the sheath, and the other end is connected to the cable that slides in the fore-and-aft direction in the sheath. Thus, the endoscopic snare is so structured that only one side connected to the cable is pushed out and projected from the sheath. Therefore, the projected snare loop assumes an asymmetric and non-oblong ring shape in which the expanding direction is naturally deviated on either side about the axis of the sheath already in the early stage of projection. The ring shape expanded in this manner varies in size depending on the projecting length of the snare loop, but can keep the ring shape without leading significant difference in the ratio between the diameter in the length direction and the diameter in the width length irrespectively of this size.

Since the distal end tip to which one end of the snare loop is attached is disposed in the distal end part of the sheath, the root part of the snare loop that forms a ring shape at the time of expansion is twisted, and the interval in the root part is reduced. Also, since the snare loop is not provided with a protruding portion, the current-carrying part can be brought into contact with the entire circumference of the polyp when the polyp is captured. When the distance between the distal end surface of the distal end tip and the distal end of the sheath becomes long (larger than 5 mm), the interval in the root part of the snare loop can increase depending on the situation when the snare loop is expanded. This increases the part that is not in contact with the polyp circumference at the time of capturing, and leads the concern that the uniform cauterization is not enabled.

According to the endoscopic snare of the present invention, it is possible to form a ring loop that is less susceptible to the shape variation irrespectively of the projecting length of the snare loop when the snare loop is projected from the sheath. This makes it possible to capture various sizes of polyps, in particular, a small polyp easily and stably. Also, a polyp can be captured at a position that is easily viewable from the endoscopic camera, so that excision can be carried out more stably.

Further, when a polyp is captured, the current-carrying part comes into contact with the circumference of the polyp without any gap, so that uniform cauterization is achieved and thus secure and stable thermocauterectomy is enabled.

DETAILED DESCRIPTION OF PREFERRED EMBODIMENTS

Hereinafter, an embodiment of the present invention will be described with reference to the drawings.

Figure 1:
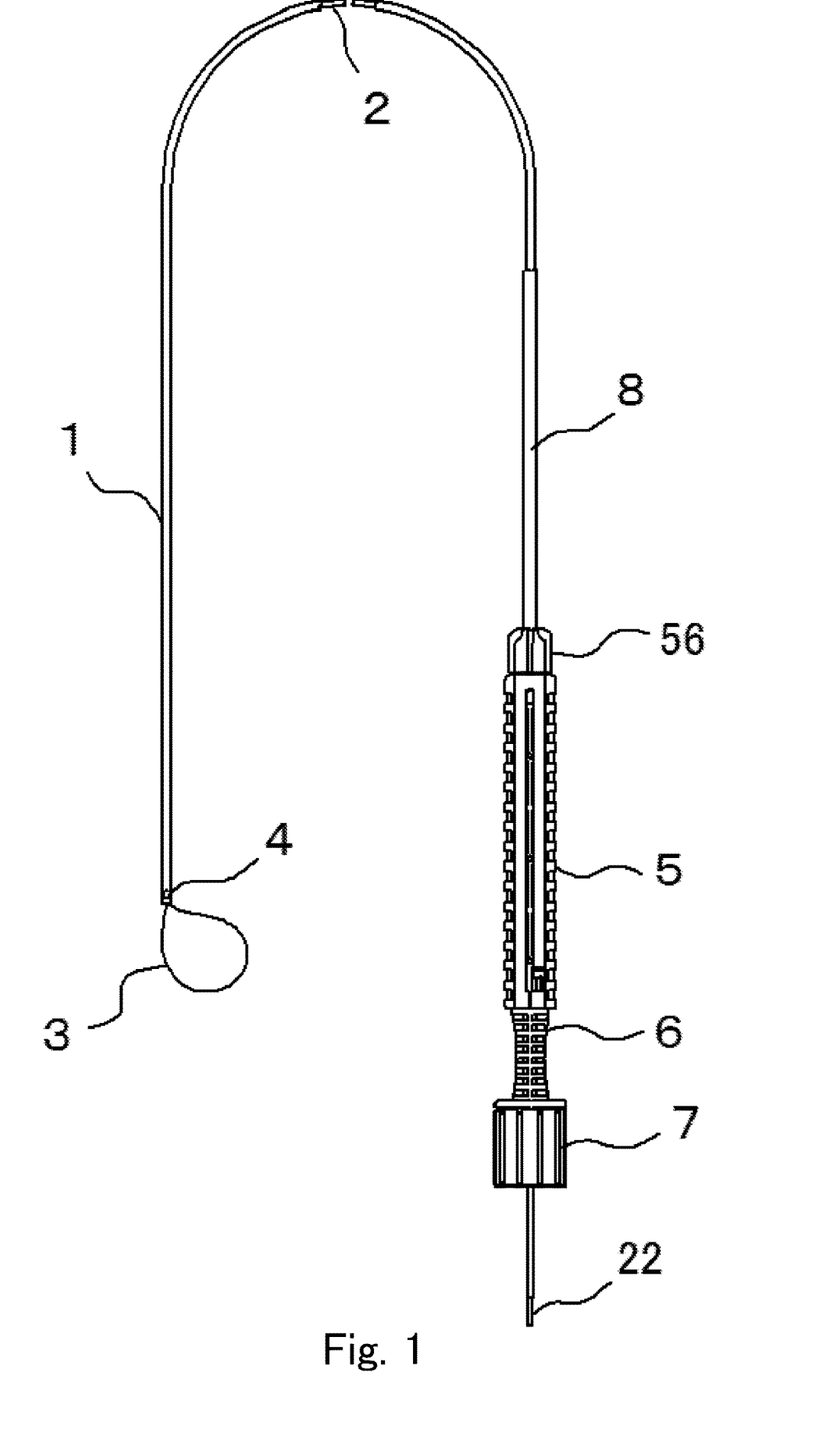
FIG. 1 is an overall configuration view showing an endoscopic snare in an embodiment of the present invention.
Figure 2:
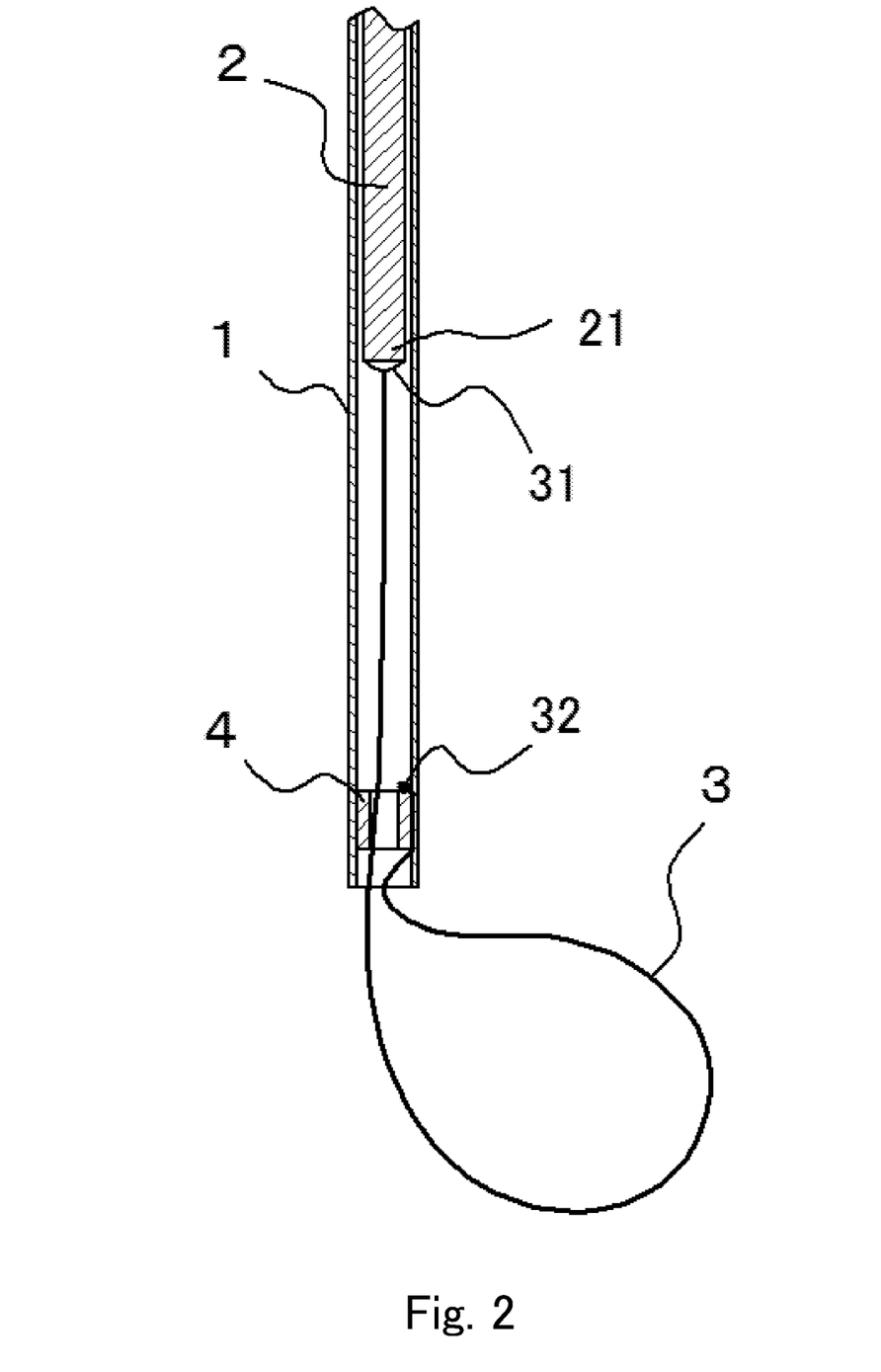
FIG. 2 is an enlarged view showing a distal end part in the embodiment.

FIG. 1 is an overall configuration view showing an endoscopic snare in the present embodiment, and FIG. 2 shows a distal end part on the side of the snare loop thereof.

The endoscopic snare of the present embodiment includes:

an elongated sheath 1 having flexibility that can be inserted into a forceps channel of an endoscope;

a cable 2 disposed inside the sheath and sliding to face the sheath 1 in an axial direction;

a snare loop 3 formed of a metal wire, which has one end connected to a cable distal end 21 at a first wire attaching portion 31 and has the other end retained by a later-described distal end tip 4 at a second wire attaching portion 32 to form a string of loop;

a distal end tip 4 disposed in the distal end part of the sheath 1 and retaining one end of the snare loop 3; and a hand operating part made up of a sheath base 5 connected to the sheath 1, and a cable base 6 connected to the cable 2, for operating the snare loop 3 by a hand via the cable 2.

As the sheath 1, a flexible, but relatively hard material having small extensibility in the axial direction and small skin friction resistance is used in consideration of the insertion into a forceps channel and the operability of the snare. For example, an external cylinder tube formed of a resin such as polypropylene or a fluorine resin and having a size suited for the endoscopic forceps channel can be selected. In this example, a polypropylene resin tube having an outer diameter of 2.6 mm and a length of 1600 mm (effective length) that can be naturally used in a common forceps channel is employed. A rear end part is formed to be open in a flared shape as a connection end 11 to the later-described sheath base 5.

The cable 2 desirably has both appropriate flexibility and stiffness in consideration of the operability in the forceps channel, and has small extensibility in the axial direction and further has torque properties capable of securely transmitting a hand operation to the distal end. In the present embodiment, the cable 2 is formed of a metallic stranded wire formed by stranding a plurality of metallic wires of stainless or the like. The cable 2 is formed to have such an outer diameter (in this example, 1.5 mm) that allows the cable 2 to fit with the sheath 1 and slide in the sheath lumen normally. At the distal end part 21, an end part on one side of the snare loop 3 and the first wire attaching portion 31 are connected by brazing or the like. The rear end side is connected with the later-described cable base 6, and the terminal end part thereof is extended to penetrate the cable base 6, which constitutes a terminal connecting part 22 to a high-frequency wave generator (not illustrated).

The snare loop 3 is formed of a stranded wire obtained by stranding a plurality of metallic thin wires of stainless or the like having a smaller diameter than the cable 2, or a current-carriable metallic wire that is memorized to assume a developed loop shape in a natural state and is less susceptible to deformation such as collapse, creases or the like due to deterioration with age even when the snare loop 3 is stored inside the thin sheath 1 (for example, super-elastic alloy such as Ni—Ti alloy). Thus, the snare loop 3 is designed to expand and naturally extend in a ring shape when it is pushed out from the sheath 1. As the snare loop 3, a straight wire without projections and depressions such as a protrusion at a distal end part that is often seen in a conventional snare is used. The snare loop 3 is configured to come into contact with the circumference of a polyp without any gap when it captures the polyp. In the present embodiment, a metallic stranded wire formed by stranding seven stainless thin wires of 0.2 mm that is less susceptible to the shape change is used.

One end part of the metallic stranded wire is connected to the cable distal end 21 by brazing or the like at the first wire attaching portion 31, and is set so that advance or retraction in the fore-and-aft direction is enabled by the sliding operation of the cable 2. The other end part is retained at the second wire attaching portion 32 by a later-described distal end tip 4 disposed in the distal end part of the sheath 1, and is set to remain at a specific position in the distal end part of the sheath. Thus, the snare loop 3 is formed. In this example, a part for retaining the snare loop 3 to the distal end tip 4 is designed as a part that achieves retention by tucking one end side of the snare loop 3 through the gap between the inner surface of the sheath 1 and the distal end tip 4, and forming a knot in the end part of the snare loop 3 for preventing the snare loop 3 from coming off.

With such a configuration of the snare loop 3, the shape formed by the snare loop 3 when the snare loop 3 projects out of the distal end of the sheath 1 is not symmetric about the axis of the sheath 1 but is asymmetric with the expansion deviated on the side of the second wire attaching portion 32. Further, a substantially ring loop that is not oblong both in the length direction and the width direction is naturally formed, and the outline of the basic ring shape is maintained from the early stage of projection to the maximumly projected stage.

The distal end tip 4 is a cylindrical tip with a lumen formed of metal or a resin, and is disposed in the state that it is retained inside the distal end part of the sheath 1. One end side of the snare loop 3 penetrates through the lumen, and is connected to the distal end of the cable 2. The other end side of the snare loop 3 is tucked in the gap between the inner surface of the sheath 1 and the distal end tip 4 in the manner as described above, and is retained by a knot at the second wire attaching portion 32 so as not to come off from the attaching portion 32. With regard to disposure of the distal end tip 4 in the sheath 1, the distal end surface of the tip 4 is preferably disposed at the position as close as possible to the distal end side from the distal end part of the sheath 1 (at least within 5 mm) insofar as storage of the snare loop 3 in the sheath is not interfered. It is experimentally recognized that the interval of the root part of the ring shape when the snare loop 3 is expanded is smaller when the distal end tip 4 is disposed on the distal end side as described above, compared with the case where it is disposed far from the distal end. Therefore, the current-carrying part is brought into contact with the circumference of the polyp without any gap, and uniform thermocauterectomy can be conducted.

Figure 3A:
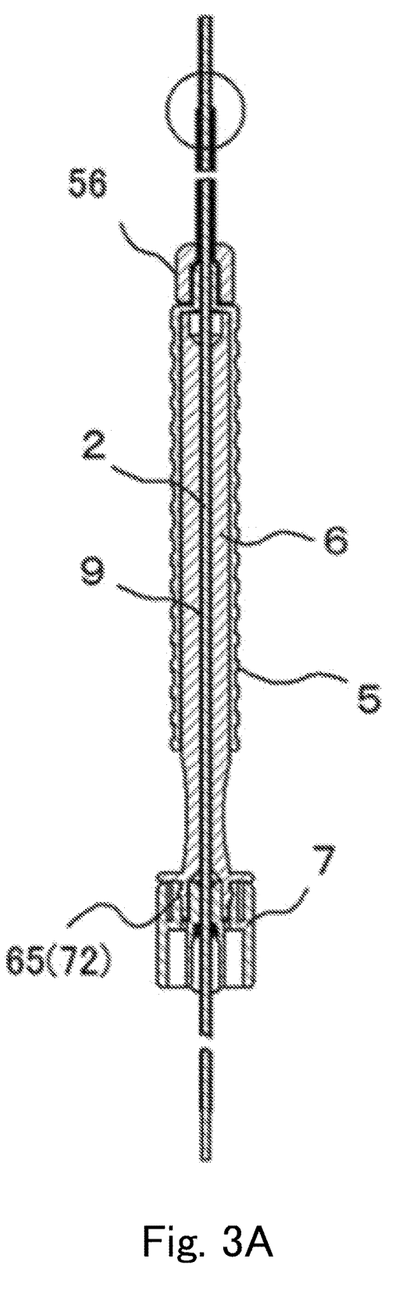
FIG. 3A is an enlarged view showing an entire hand operating part in the embodiment.
Figure 3B:
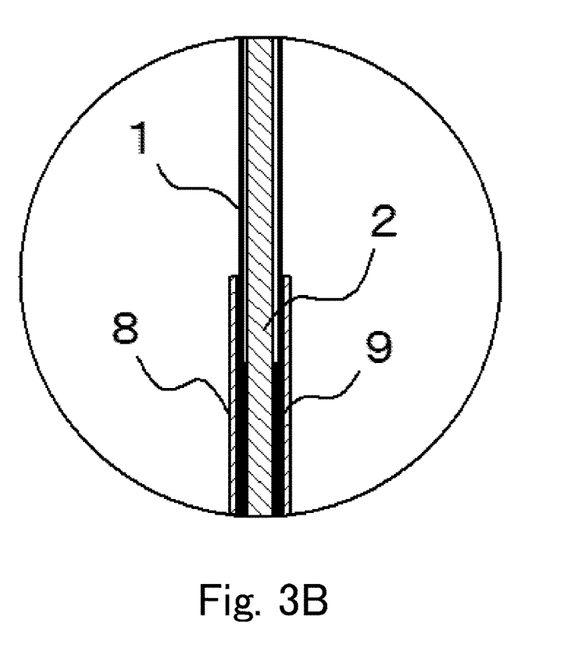
FIG. 3B is an enlarged view of circled part shown in FIG. 3A.
Figure 4:
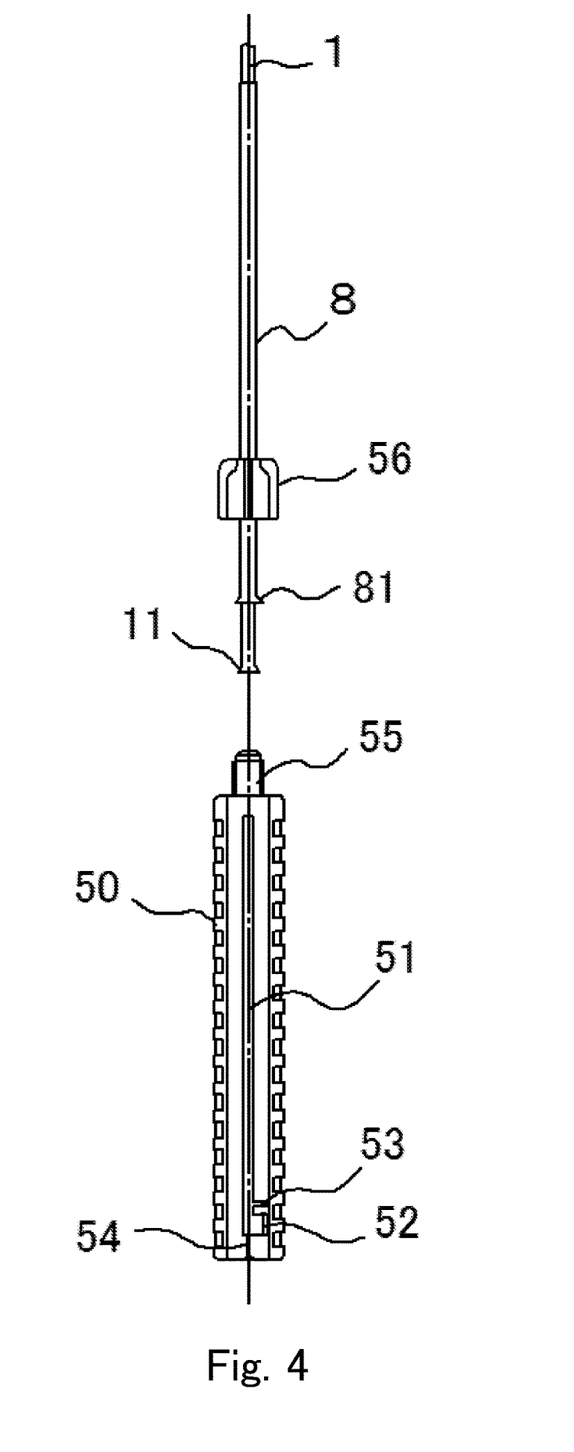
FIG. 4 is a configuration view showing a sheath base in the hand operating part in the embodiment.
Figure 5A:
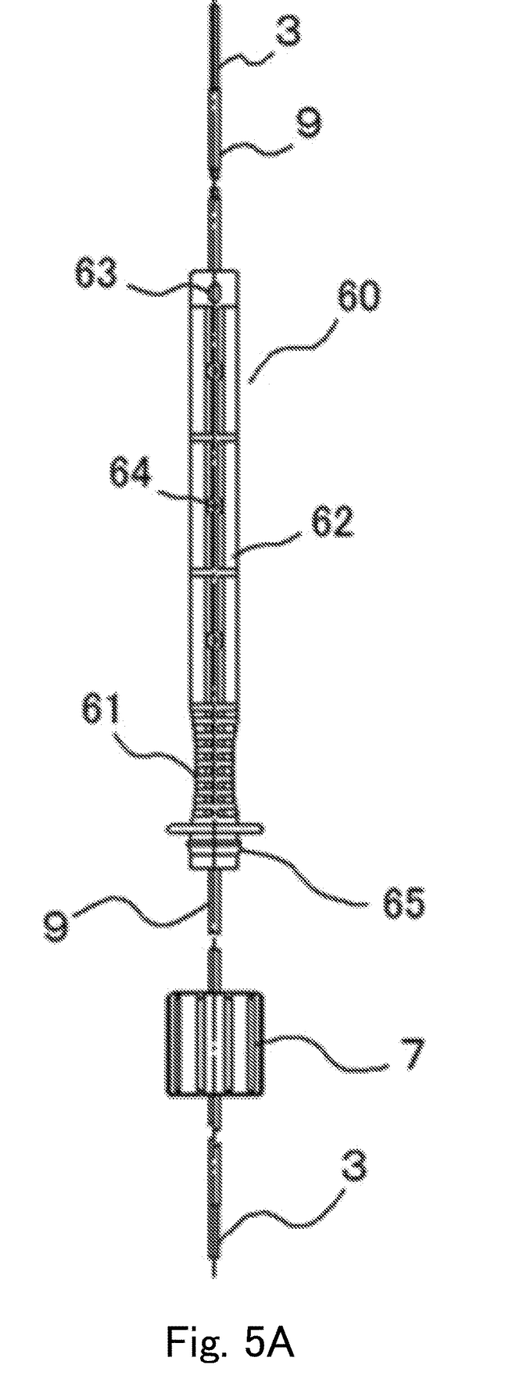
FIG. 5A is a configuration view showing a cable base in the hand operating part in the embodiment.
Figure 5B:
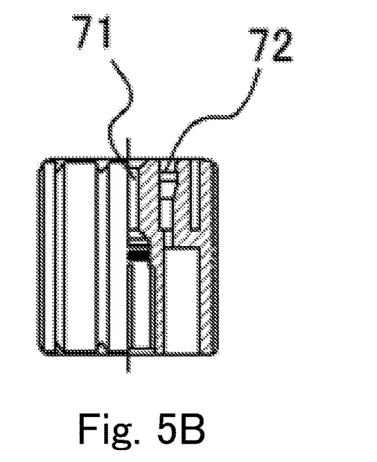
FIG. 5B is a configuration view showing a cable base ring of the cable base shown in FIG. 5A.

FIG. 3A shows the entire hand operating part in the present embodiment. FIG. 3B is an enlarged view of circled part shown in FIG. 3A. FIG. 4 shows a sheath base of the hand operating part. FIG. 5A and FIG. 5B show a cable base. FIG. 5A shows the entirety and FIG. 5B shows a cable base ring.

The hand operating part includes the sheath base 5 made up of a sheath base body 50 connecting to the rear end part of the sheath 1 to form a gripping part, and a cap 56, and the cable base 6 made up of a cable base body 60 connecting to the rear end part of the cable 2 to form an operating part for operating the snare loop 3 by a hand, and a cable base ring 7.

The sheath base body 50 is an elongated cylindrical body formed of a resin mold, into which the cable base body 60 is inserted in a slidable manner. At the distal end part of the cylindrical body, a male screw 55 is formed for connecting a reinforcing tube 8, which prevents bending and the like of the sheath 1 and the sheath terminal side, to the sheath base body 50. The male screw 55 and the connection cap 56 formed with a female screw corresponding to the male screw 55 are fastened while the sheath connection end 11 having a flared shape, and an open part of a reinforcing tube connection end 81 having a similar flared shape are sandwiched therebetween, and thus the sheath 1 and the reinforcing tube 8 are connected to the sheath base body 50. On the lateral surface of the cylindrical body, a slit 51 for sliding the cable base body 60 straight in the axial direction is provided. At the rear end part of the slit 51, a locking part 52, which locks the cable base body 60 by meshing while the cable base body 60 is slightly revolved, is formed. Also, in the sheath base body 50, a cut 54 for communicating with the slit 51 to allow a later-described locking protrusion 63 of the cable base body 60 to pass through the slit 51, and a roll off 53 for fitting the locking protrusion 63 into the locking part 52 are formed.

The cable base body 60 is made up of a sliding part 62 in the form of a rod cylinder to be inserted into the lumen of the sheath base body 50 in a slidable manner, and a gripping part 61 to serve as an operating part on the rear end side, and has a channel for letting the cable 2 penetrate, and letting a guide pipe 9 for protecting the cable 2 on the side of the cable base 6 penetrate. The distal end part of the lateral surface of the sliding part 62 is provided with a locking protrusion 63 that slides in the axial direction of the cylinder body in engagement with the slit 51 of the sheath base body 50, and is fitted into the locking part 52. Further, in the present embodiment, a plurality of guiding protrusions 64 are provided on the same axial line of the locking protrusion 63.

According to the above configuration, since the locking protrusion 63 of the cable base body 60 slides along the slit 51 of the sheath base body 50 in developing or storing the snare loop 3, the action in the axial direction and in the circumferential direction is restricted.

Also, the gripping part 61 is provided with a rotary sliding receiving part 65 which serves as a part that can be rotatably connected to the later-described cable base ring 7.

In the cable base ring 7, the cable 2 and the guide pipe 9 are connected to a cable connecting part 71 on the side of the ring distal end by adhesion or the like. The rotary sliding receiving part 65 of the cable base body 60, and a rotary sliding part 72 of the cable base ring 7 are fitted rotatably and slidably.

In the above configuration, the cable 2 is connected to the cable base ring 7, and is rotatable and slidable with the cable base body 60. Therefore, the orientation of the snare loop 3 can be varied slightly only by a rotating operation of the cable base ring 7 without rotating the sheath base 5 (sheath 1) or the cable base body 60, although twisting occurs in the snare loop 3.

Figure 6A:
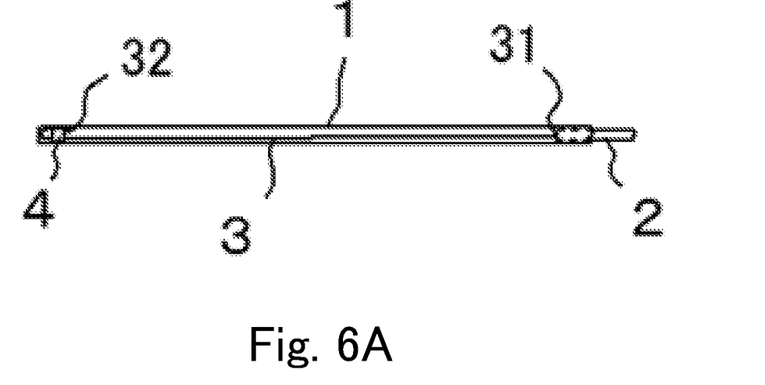
FIG. 6A is a view for describing variation by expansion of a snare loop in the embodiment and shows the distal end part in the state that the snare loop is stored in the sheath.
Figure 6B:
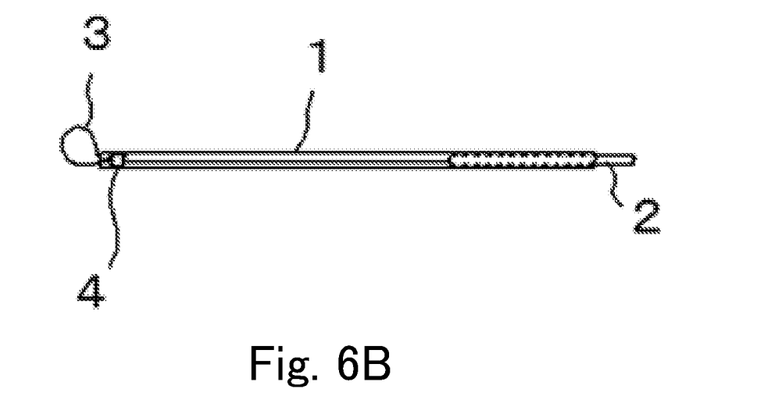
FIG. 6B is a view for describing variation by expansion of a snare loop in the embodiment and shows the distal end part in the early stage of projection of the snare loop.
Figure 6C:
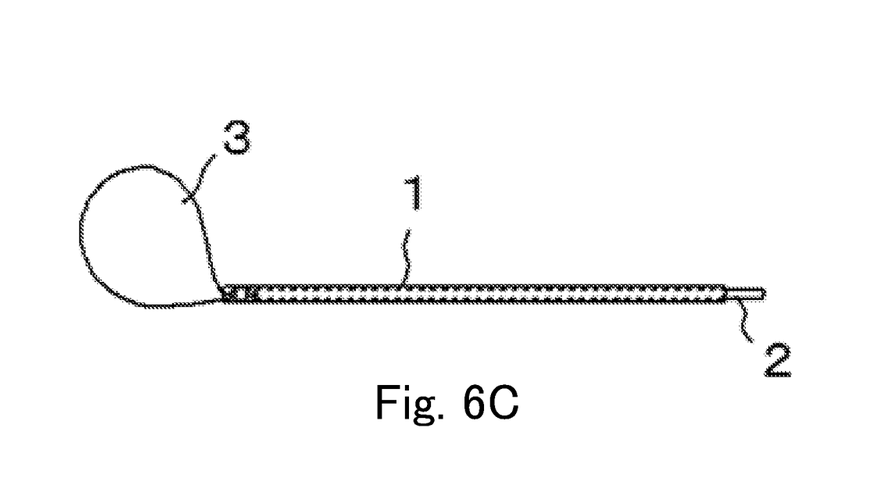
FIG. 6C is a view for describing variation by expansion of a snare loop in the embodiment and shows the distal end part in the state that the snare loop is projected maximumly.
Figure 7A:
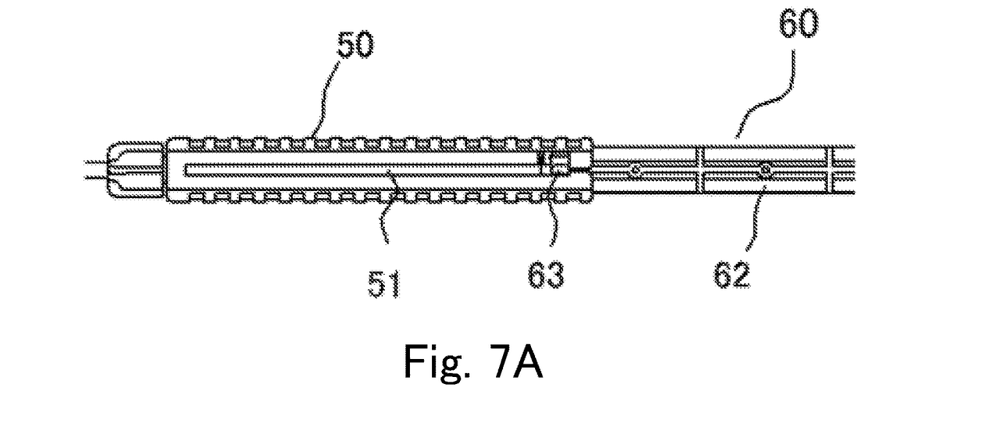
FIG. 7A is a view for describing variation by pushout of a base part in the embodiment and shows the state of the hand operating part corresponding to FIG. 6A.
Figure 7B:
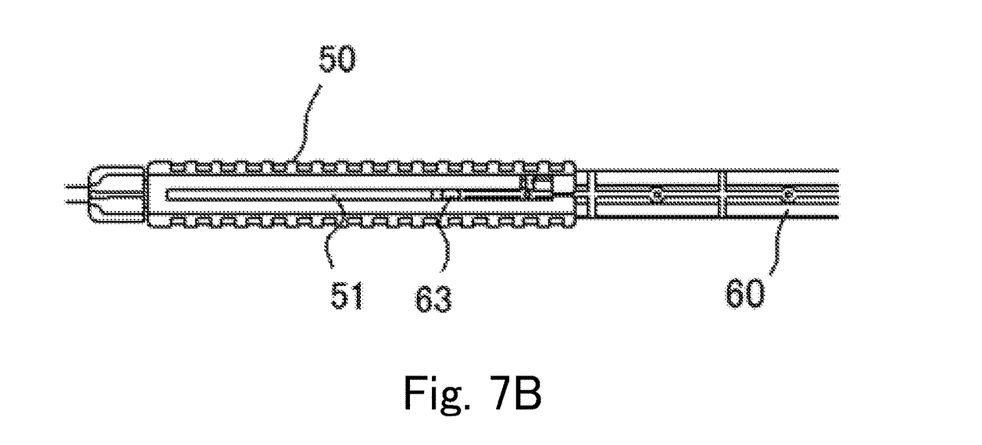
FIG. 7B is a view for describing variation by pushout of a base part in the embodiment and shows the state of the hand operating part corresponding to FIG. 6B.
Figure 7C:
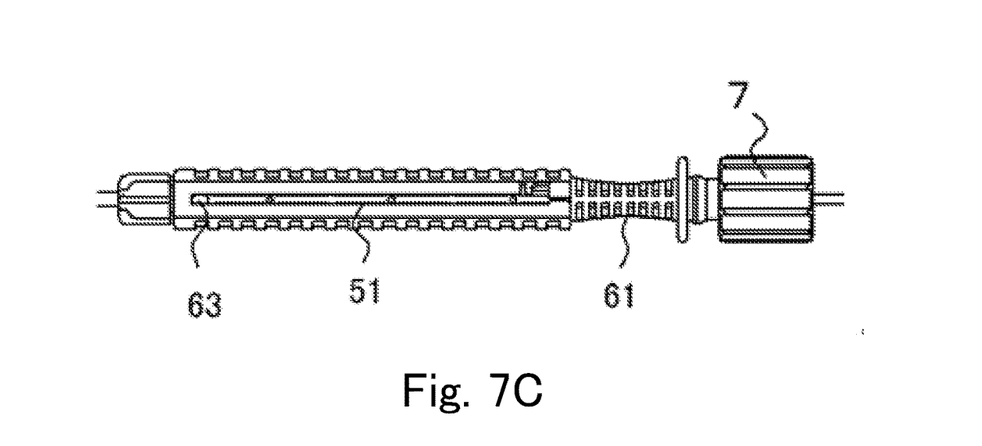
FIG. 7C is a view for describing variation by pushout of a base part in the embodiment and shows the state of the hand operating part corresponding to FIG. 6C.

FIG. 6A, FIG. 6B and FIG. 6C are views for describing the shape variation depending on the projecting length of the snare loop 3 from the sheath 1 in the present embodiment, and FIG. 7A, FIG. 7B and FIG. 7C are views for describing hand operating parts corresponding to the shape variation. FIG. 6A shows the distal end part in the state that the snare loop is stored in the sheath, and FIG. 7A shows the state of the hand operating part corresponding to this. FIG. 6B shows the distal end part in the early stage of projection of the snare loop, and FIG. 7B shows the state of the hand operating part corresponding to this. FIG. 6C shows the distal end part in the state that the snare loop is projected maximumly, and FIG. 7C shows the state of the hand operating part corresponding to this.

In the present embodiment, one end part of the stranded wire forming the snare loop 3 is retained at the second wire attaching portion 32 by the distal end tip 4 disposed in the distal end part of the sheath 1, and the other end part is connected to the sliding cable distal end 21 at the first wire attaching portion 31. Therefore, the snare loop 3 is configured to advance or retract from the sheath 1 by the hand operation as described below.

When the snare loop 3 is stored in the sheath 1, for example, during insertion into a forceps channel, the cable base body 60 is drawn rearward maximally from the sheath base body 50, the locking protrusion 63 is positioned in the rear end part of the slit 51, and the cable 2 is drawn into the sheath 1 by the distance corresponding to the length of the slit 51 (see FIG. 6A, and FIG. 7A).

As the cable base body 60 is slid forward from this state while the sheath base body 50 is retained, the cable 2 advances in the sheath 1, and the snare loop 3 projects from the sheath 1. At this time, due to the configuration as described above, the snare loop 3 is projected straight only on one side connected to the side of the cable 2. Since the side connected to the distal end tip 4 is fixed, the snare loop 3 is twisted and deformed into an S-shape (see FIG. 2) or the like. This reduces the gap in the root part positioned in the distal end part of the sheath 1, and the snare loop 3 is expanded naturally into a ring shape in which, as the shape as a whole, the diameter in the length direction and the diameter in the width direction do not significantly differ from the early stage of projection from the sheath 1. Also, the snare loop 3 is expanded in a deviated loop shape that is asymmetric about the central axis of the sheath 1 and expands in the direction where the second wire attaching portion 32 is present (see FIG. 6B and FIG. 7B).

Thus, the snare loop 3 of the present embodiment assumes a ring shape where the diameter in the length direction is not significantly different from the diameter in the width direction, and is deviated with respect to the axis of the sheath 1. Therefore, when the cable base body 60 is further advanced and the snare loop 3 is further pushed out, the outline of the basic ring form of the snare loop 3 is not varied except that the size of the ring is gradually increased depending on the pushout length, even though some twisting or strain occurs (see FIG. 6C, and FIG. 7C).

What is claimed is:

1. An endoscopic snare comprising:
    a flexible sheath having a distal end opening at a distal end part of the sheath;
    a cable configured to slide in the sheath, the cable having a distal end;
    a snare loop having a first end connected to the distal end of the cable, the snare loop projecting from or retracting into the distal end opening of the sheath;
    a cylindrical distal end tip disposed entirely within the flexible sheath and having a distal end surface spaced from the distal end opening of the sheath and retaining a second end of the snare loop at a specific position in the distal end part of the sheath by attachment of the second end of the snare loop to a back side of the distal end tip with part of the snare loop tucked through a gap between an inner surface of the sheath and a lateral side of the distal end tip, where the snare loop penetrates through an axial lumen defined in the distal end tip; and
    a hand operating part for operating the snare loop via the cable, wherein
    the snare loop is expanded into an asymmetric ring shape without a protruding portion when being projected from the distal end opening of the flexible sheath, where expansion of the snare loop is deviated to either side about an axis of the sheath.

2. The endoscopic snare according to claim 1, wherein the snare loop is formed of a metallic stranded wire.

3. The endoscopic snare according to claim 2, wherein the distal end surface of the distal end tip is disposed at a position within 5 mm from the opening in the distal end part of the sheath.

4. The endoscopic snare according to claim 1, wherein the distal end surface of the distal end tip is disposed at a position within 5 mm from the opening in the distal end part of the sheath.

* * * * *

UNITED STATES PATENT AND TRADEMARK OFFICE
CERTIFICATE OF CORRECTION

| | | |
|---|---|---|
| PATENT NO. | : 11,241,249 B2 | |
| APPLICATION NO. | : 15/421546 | |
| DATED | : February 8, 2022 | |
| INVENTOR(S) | : Kiyokazu Nakajima et al. | |

It is certified that error appears in the above-identified patent and that said Letters Patent is hereby corrected as shown below:

On the Title Page

Item (73), add first named Assignee -- Osaka University, Osaka, Japan --.

Signed and Sealed this
Eighth Day of November, 2022

Katherine Kelly Vidal
*Director of the United States Patent and Trademark Office*